(12) United States Patent
Hou et al.

(10) Patent No.: US 6,860,393 B2
(45) Date of Patent: Mar. 1, 2005

(54) FILTER DEVICE AND FILTER ELEMENT COMPRISING AT LEAST ONE NEGATIVELY CHARGED MEMBRANE

(75) Inventors: Chung-Jen Hou, Pensacola, FL (US); Peter Konstantin, Boulder, CO (US); Yujing Yang, Newton, MA (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 10/895,048

(22) Filed: Jul. 21, 2004

(65) Prior Publication Data

US 2004/0262216 A1 Dec. 30, 2004

Related U.S. Application Data

(63) Continuation of application No. 09/914,165, filed as application No. PCT/US00/04745 on Feb. 25, 2000, now Pat. No. 6,783,937.
(60) Provisional application No. 60/121,668, filed on Feb. 25, 1999.

(51) Int. Cl.$^7$ .................. B01D 63/14; B01D 63/10; B01D 67/00; B01D 71/00
(52) U.S. Cl. .......... 210/435; 210/483; 210/490; 210/493.1; 210/497.01; 210/497.1; 210/500.35; 210/500.38; 210/500.41; 210/512.1; 264/41; 427/244
(58) Field of Search .................. 210/435, 483, 210/490, 493.1, 497.01, 497.1, 512.1, 500.35, 500.38, 500.41; 264/41; 427/244

(56) References Cited

U.S. PATENT DOCUMENTS

| | | |
|---|---|---|
| 4,455,370 A | 6/1984 | Bartelsman et al. |
| 4,617,321 A | 10/1986 | MacDonald |
| 5,021,160 A | 6/1991 | Wolpert |
| 5,783,094 A | 7/1998 | Kraus et al. |
| 5,843,789 A | 12/1998 | Nomura et al. |

FOREIGN PATENT DOCUMENTS

| | | |
|---|---|---|
| DE | 44 39 444 A1 | 5/1996 |
| EP | 0 474 617 A1 | 3/1992 |
| WO | WO 96/14151 | 3/1996 |
| WO | WO 98/17377 | 4/1998 |

*Primary Examiner*—John Kim
(74) *Attorney, Agent, or Firm*—Leydig, Voit & Mayer, Ltd.

(57) ABSTRACT

The present invention provides, in certain embodiments, a negatively charged microporous membrane comprising a porous substrate and a crosslinked coating having fixed negative charges. The crosslinked coating can be prepared, e.g., from a polymerized composition comprising an unsaturated monomer having an anionic group, an N-(hydroxymethyl)- and/or N-(alkoxymethyl)-acrylamide, a hydrophilic unsaturated monomer, and an initiator. The present invention further provides, in some embodiments, a negatively charged microporous membrane comprising a porous substrate and a crosslinked coating prepared from a polymerized composition comprising an unsaturated monomer having an anionic group, an N-(hydroxymethyl)- or N-(alkoxymethyl)-acrylamide, a polysaccharide, and an initiator. The membranes of the present invention are suitable for use in ion exchange chromatography, for example, in the separation and purification of positively charged species such as proteins.

16 Claims, 3 Drawing Sheets

FILTER DEVICE AND FILTER ELEMENT COMPRISING AT LEAST ONE NEGATIVELY CHARGED MEMBRANE

CROSS-REFERENCE TO A RELATED APPLICATION

This application is a continuation of U.S. patent application Ser. No. 09/914,165, filed on Dec. 12, 2001 issued as U.S. Pat. No. 6,783,937 which is a 371 of PCT/US00/04745, filed on Feb. 25, 2000. This application claims priority from U.S. Provisional Patent Application No. 60/121,668, filed on Feb. 25, 1999, the disclosure of which is incorporated herein by reference in its entirety.

FIELD OF THE INVENTION

The present invention generally relates to negatively charged membranes, and in particular to negatively charged membranes comprising a porous substrate and a crosslinked coating. The membranes find use in the treatment of fluids containing positively charged species such as proteins, e.g., in ion-exchange chromatography.

BACKGROUND OF THE INVENTION

Negatively charged ion-exchange membranes have been proposed for the separation and/or purification of biomolecules such as proteins, amino acids, and nucleic acids. For the ion exchange membrane to perform effectively in the above applications, the membrane should satisfy several important parameters. For example, the membrane should exhibit high rates of fluid flow. The membrane should have high dynamic binding capacity for biomolecules, and should be capable of selectively binding the biomolecules, which have different surface charges. The membrane should, therefore, have low non-specific binding, e.g., resulting from hydrophobic interactions. The membrane should withstand high treatment fluid velocities. The preparation of the membrane should not involve chemistries and processes that are cumbersome to practice. Some of the cation exchange membranes known heretofore suffer from the failure to satisfy one or more of the parameters set forth above.

Accordingly, there exists a need for a cation exchange membrane that exhibits high rates of fluid flow. There further exists a need for a cation exchange membrane that has high dynamic binding capacity and selectivity for biomolecules. There further exists a need for a membrane that has low non-specific binding or low binding that results from hydrophobic interactions. There further exists a need for a membrane that can withstand high fluid flow velocities. There further exists a need for a membrane that involves preparation chemistries and/or processes that are not cumbersome to practice.

These advantages of the present invention, as well as additional inventive features, will be apparent from the description of the invention provided herein.

BRIEF SUMMARY OF THE INVENTION

Figure 1:
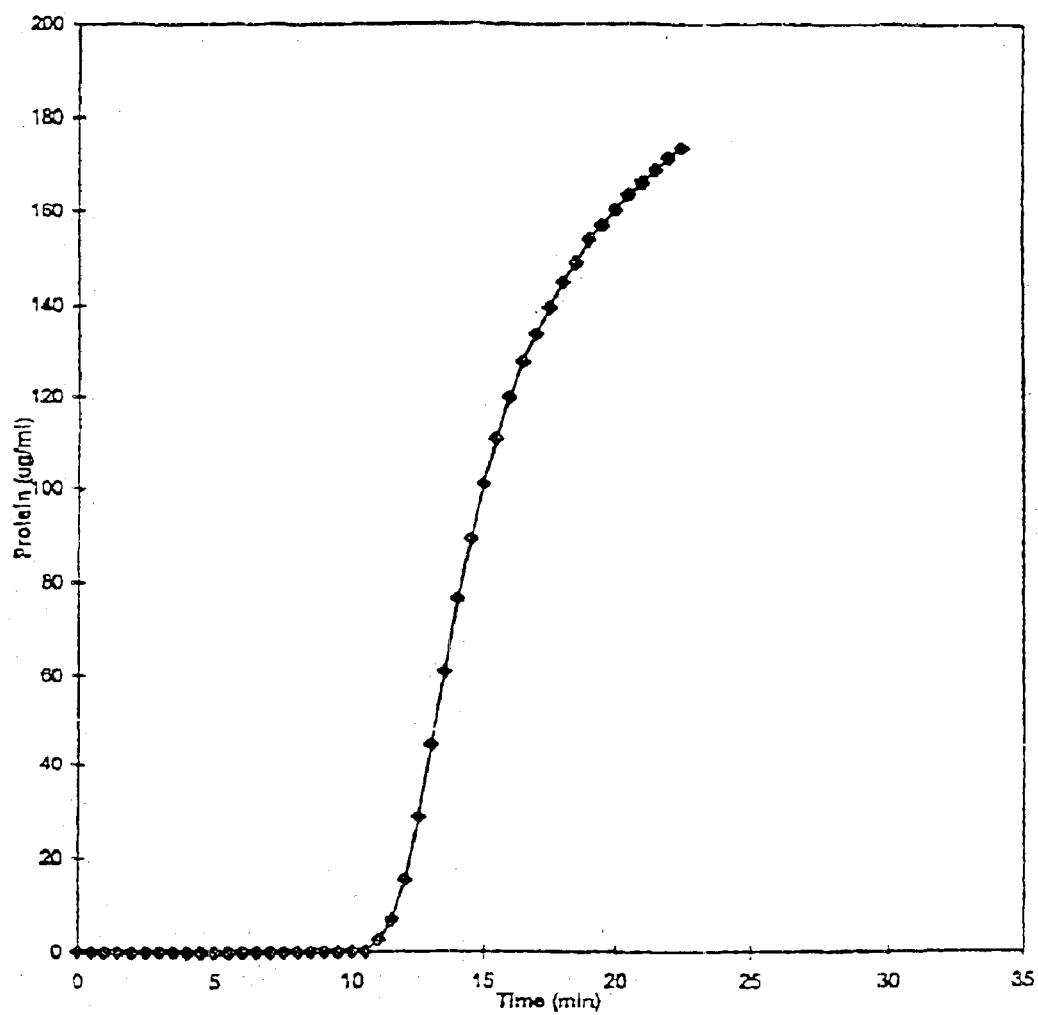
FIG. 1 depicts the breakthrough curve for lysozyme obtained on an embodiment membrane of the present invention. The x-axis represents the filtration time, and the y-axis represents the absorbance of the filtrate at 280 nm and is indicative of the concentration of the protein. See Example 2 for additional details.

Many of the foregoing needs have been fulfilled by the present invention which provides a negatively charged microporous membrane comprising a porous substrate and a crosslinked coating having negatively charged groups. In a preferred embodiment, the membrane can be prepared from a polymerized composition comprising an unsaturated monomer having an anionic group, at least one or more N-(hydroxyalkyl)- and/or N-(alkoxyalkyl)-acrylamides, and a hydrophilic unsaturated monomer.

The present invention further provides a negatively charged microporous membrane comprising a porous substrate and a crosslinked coating prepared from a hydroxyl-rich material such as a polysaccharide and a polymerized composition comprising an unsaturated monomer having an anionic group, at least one or more N-(hydroxymethyl)- and/or N-(alkoxymethyl)acrylamides, and an initiator.

The present invention further provides a negatively charged microporous membrane having a protein binding capacity of about 25 mg/ml lysozyme or more comprising a porous substrate and a crosslinked coating that provides a fixed negative charge. The present invention further provides a negatively charged microporous membrane comprising a porous substrate and a crosslinked coating comprising a polymer having anionic groups and amide—amide and amide-ester crosslinks.

The membranes of the present invention are advantageously free of covalent bonds or grafts with the substrate.

The present invention further provides a process for preparing an embodiment of the membrane comprising coating a porous substrate with a polymerized composition comprising an anionic group and curing the membrane. The membrane can be optionally washed or leached to remove extractable residue therein.

The present invention further provides devices, e.g., filter devices, chromatographic devices, macromolecular transfer devices, and membrane modules comprising the membranes of the present invention. The present invention further provides a process for separating a positively charged material such as positively charged atoms, molecules, and particulates, and, preferably, biomolecules, from a fluid, the process comprising placing the fluid in contact with the negatively charged microporous membrane so as to adsorb the positively charged material to the membrane. The present invention further provides a process for treating a fluid containing positively charged materials comprising contacting the fluid with a membrane of the present invention and selectively releasing the positively charged materials. The present invention further provides a process for transferring macromolecules from a device or element such as an electrophoresis gel comprising contacting the gel with the membrane of the present invention and transferring the biomolecules to the membrane.

While the invention has been described and disclosed below in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

The present invention provides embodiments of negatively charged membranes having high charge density, high water flow rates, high dynamic protein binding capacity, and low non-specific protein binding capacity. The membranes of the present invention find use in cation exchange chromatography and in the separation and/or purification of charged species, especially biomolecules such as proteins.

The present invention provides, in some embodiments, a negatively charged microporous membrane comprising a porous substrate and a crosslinked coating having anionic groups. The crosslinked coating can be prepared from a polymerized composition comprising an unsaturated monomer having an anionic group, at least one or more N-(hydroxyalkyl)- or N-(alkoxyalkyl)-acrylamides, a hydrophilic unsaturated monomer. The composition can further include an initiator. In preferred embodiments, the N-(hydroxyalkyl)- or N-(alkoxyalkyl)-acrylamide is one wherein the alkyl moiety has 4 or less carbon atoms, and more preferably the alkyl moiety is methyl.

In certain embodiments, the membrane comprises a porous substrate and a crosslinked coating prepared from a polymerized composition comprising an unsaturated monomer having an anionic group, at least one or more N-(hydroxymethyl)- and/or N-(alkoxymethyl)-acrylamides, a hydroxyl-rich material such as a polysaccharide, and optionally an initiator. The present invention further provides a negatively charged microporous membrane comprising a porous substrate and a crosslinked coating comprising a polymer having anionic groups and amide—amide and amide-ester crosslinks.

The membrane of the present invention contains fixed anionic groups. The anionic group can be any negatively charged group—sulfonic, carboxylic, phosphonic, and the like, preferably sulfonic or carboxylic acid groups. The coating composition comprises an unsaturated monomer having an anionic group. Any suitable unsaturated monomer—vinyl, vinyl aromatic, acrylic, or other monomer can be used.

The unsaturated monomer preferably is an acrylic monomer. The acrylic monomer can be an acrylate or an acrylamide. The acrylic monomer is preferably an acrylamide. The term "acrylamide" herein refers to unsubstituted as well as substituted monomers having a —C=C—(C=O)—N— moiety. The nitrogen and the C=C carbon atoms can be attached to hydrogen or other nonpolar substituents. An example of such substituents is alkyl. Thus, the substituted acrylamide can be alkylacrylamide. The term "alkyl" herein refers to an alkyl group having from 1 to about 10 carbon atoms, preferably from 1 to about 6 carbon atoms, and more preferably from 1 to about 3 carbon atoms. An example of an acrylamide monomer having a sulfonic acid group is acrylamido-N-alkylsulfonic acid, preferably 2-acrylamido-2-methyl-1-propanesulfonic acid. Preferred examples of acrylic monomers having a carboxylic acid group are 3-acrylamido-3-methylbutanoic acid (AMBA), 2-acrylamidoglycollic acid, and β-carboxyethyl acrylate.

In certain embodiments, the coating composition comprises a hydrophilic unsaturated monomer, e.g., a non-ionic hydrophilic unsaturated monomer. Any suitable hydrophilic unsaturated monomer can be used, preferably an acrylic monomer. The monomer contains one or more polar groups that contribute hydrophilicity. Examples of such groups include hydroxy, alkoxy, hydroxyalkyl, and amido. Preferred hydrophilic groups are hydroxyl and hydroxyalkyl. Thus, preferred hydrophilic acrylic monomers are hydroxyacrylic and hydroxyalkylacrylic. The acrylic monomer can be an acrylate ester or an acrylamide. An example of a preferred hydroxyalkyl acrylate monomer is hydroxypropyl methacrylate.

The coating composition comprises a crosslinking agent. Any suitable crosslinking agent known to those of ordinary skill in the art can be used. Preferred crosslinking agents include N-(alkoxymethyl)acrylamide and N-(hydroxymethyl)acrylamide. N-(isobutoxymethyl) acrylamide is further preferred.

The coating composition preferably comprises an initiator. Any suitable initiator—free radical initiator, photoinitiator, and the like, can be used. A free radical initiator is preferred. An example of a suitable free radical initiator is a persulfate such as ammonium persulfate.

Without being bound to any particular theory, it is believed that the use of the three monomers in certain embodiments contributes to increased spatial separation of charges. Thus, it is believed that the distance between the anionic groups is increased. This increased distance disfavors association of the anionic groups. Accordingly, inter- and/or intra-chain association of anionic group as is reduced compared to a system wherein only an anionic monomer and a crosslinking monomer are employed, particularly in a two monomer system wherein a hydrophilic or hydroxyl-rich material such as a polysaccharide is not employed. The reduced association makes the negatively charged groups available for interaction with positively charged molecules in the treated fluid. This results, for example, in enhanced dynamic protein binding capacity.

The membrane according to some embodiments is made from a coating composition that includes a hydroxyl-rich material, which may be a small molecule or a polymer having a plurality of hydroxyl groups, e.g., two, three, four or more hydroxyl groups per molecule. Examples of hydroxyl-rich materials include polysaccharides and polyvinyl alcohol, preferably polysaccharides. Without being bound to any particular mechanism, it is believed that the hydroxyl groups of the hydroxyl-rich material involve in hydrogen bonding with the fluid. The saccharide ring repeat units exert steric effects. Operation of one or both of these mechanisms results in increased charge separation among the anionic groups. The increased charge separation is believed to reduce anion association and facilitate interaction between the anionic sites and the positively charged species in the treated fluid.

Any suitable polysaccharide can be used, preferably a water soluble polysaccharide. An example of a preferred polysaccharide is dextran. The molecular weight of the dextran is below about 40,000,000, e.g., from about 10,000 to about 2,000,000, preferably from about 10,000 to about 500,000, and more preferably from about 10,000 to about 300,000. Particular examples of suitable molecular weights include 110,000 and 148,000.

The coating composition of certain embodiments can be prepared by combining and polymerizing the acrylic monomer having an anionic group, the nonionic hydrophilic monomer, a crosslinking agent, and the initiator. In some embodiments, the coating solution is prepared by combining and polymerizing the acrylic monomer having an anionic group, the polysaccharide, the crosslinking agent, and the initiator.

The polymerization can be carried out in a solvent, preferably in water or water/methanol solution. The polymerization is preferably stopped prior to the formation of a gel or excessive crosslinking. The viscosity of the polymerization solution can be monitored to control the degree of polymerization. The polymerization is carried out for any suitable length of time, e.g., for about 4 hours or more. According to certain embodiments, the polymerization is carried out for a period of from about 4 hours to about 5 hours. According to certain other embodiments, the polymerization is carried out for a period of from about 16 hours to about 24 hours. The viscosity of the solution is typically below about 2000 cps, e.g., from about 50 cps to about 500 cps, preferably from about 50 cps to about 500 cps, and more preferably from about 100 cps to about 500 cps. According to certain embodiments, the viscosity is from about 100 cps to about 250 cps.

The polymerization solution can contain the anionic acrylic monomer (A), the crosslinking agent (B), and the non-ionic hydrophilic monomer (C) in a suitable ratio. The percentage of each monomer (A, B, or C) can be from about 0.1 to 30% by weight, preferably from about 0.1 to 20% by weight.

It is believed that the crosslinked coating comprises amide-ester crosslinks that form as a result of the reaction of the nonionic hydrophilic monomer with the crosslinking agent. For example, these bonds form as a result of the reaction of the hydroxyl groups in the hydroxyalkyl acrylate with the N-(isobutoxymethyl)-acrylamide. In addition, amide—amide crosslinks also form as a result of the reaction between two N-(isobutoxymethyl)acrylamide monomers. For example, the amide-ester crosslink can have the formula:

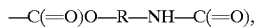
—C(=O)O—R—NH—C(=O), wherein R is divalent radical, preferably an alkoxyalkyl radical, and more preferably —CH$_2$—CH$_2$—CH$_2$—O—CH$_2$—. The amide—amide crosslink can have the formula:

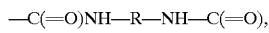
—C(=O)NH—R—NH—C(=O), wherein R is divalent radical, preferably an alkoxyalkyl radical, and more preferably —CH$_2$—O—CH$_2$—.

The coating solution contains the anionic polymer prepared as above and, optionally, a polysaccharide, preferably a dextran. The anionic polymer and the polysaccharide can be present in the coating solution in the ratio of from about 100:1 to about 1:100, preferably from about 10:1 to about 1:10, and more preferably from about 5:1 to about 1:5.

The coating solution contains the anionic polymer and, optionally dextran, in an amount of from about 0.01% to about 15% by weight, preferably from about 0.1% to about 10% by weight, and more preferably from about 0.5% to about 5% by weight of the coating solution. For example, the coating solution can contain 4.5% by weight of polymer and 1.5% by weight of dextran.

The pH of the coating solution can be adjusted suitably. For example, the pH of the coating solution containing a carboxylated polymer can be adjusted to about 3.0 to about 4.0 and preferably about 3.75. The pH of the coating can be adjusted by the addition of an acid or base. An example of a suitable base is 2N NaOH aqueous solution.

The coating solution is coated on a porous substrate, preferably a hydrophilic substrate. The hydrophilic porous substrate can be made of any suitable material; preferably, the substrate comprises a polymer. Examples of suitable polymers include polyaromatics, polysulfones, polyolefins, polystyrenes, polycarbonates, polyamides, polyimides, fluoropolymers, cellulosic polymers such as cellulose acetates and cellulose nitrates, and PEEK. Aromatic polysulfones are preferred. Examples of aromatic polysulfones include polyethersulfone, bisphenol A polysulfone, and polyphenylsulfone. Polyethersulfone is particularly preferred. The porous substrate can have any suitable pore size, for example, a pore size of below about 10 μl, e.g., from about 0.01 μm to about 10 μm, preferably from about 0.1 μm to about 5 μm, and more preferably from about 0.2 μm to about 5 μm. The porous substrate can be asymmetric or, in a preferred embodiment, symmetric.

The porous substrate can be prepared by methods known to those of ordinary skill in the art. For example, the porous substrate can be prepared by a phase inversion process. Thus, a casting solution containing the polymer, a solvent, a pore former, a wetting agent, and optionally a small quantity of a non-solvent is prepared by combining and mixing the ingredients, preferably at an elevated temperature. The resulting solution is filtered to remove any impurities. The casting solution is cast or extruded in the form of a sheet or hollow fiber. The resulting sheet or fiber is allowed to set or gel as a phase inverted membrane. The set membrane is then leached to remove the solvent and other soluble ingredients.

The porous substrate can be coated with the coating solution by methods known to those of ordinary skill in the art, for example, by dip coating, spray coating, meniscus coating, and the like. Dip coating, for example, can be carried out as follows. The substrate is immersed in the solution for a given period of time sufficient to insure complete or substantially complete coating of the pore walls. The immersion time can be from about 1 second to 1.0 minute, preferably from about 0.1 minutes to about 0.5 minutes, and more preferably from about ⅙ minute to about ⅓ minute. Following the immersion, the excess coating solution on the substrate is removed by allowing it to drain under gravity or by the use of a squeegee or air knife. The resulting coated substrate is cured to effect the curing or crosslinking of the coating composition.

Thus, the membrane can be cured below 150° C., e.g., at a temperature of from about 60° C. to about 130° C., and preferably at a temperature of from about 80° C. to about 130° C., for a suitable period of time, which can range from about 5 minutes to about 120 minutes and preferably from about 5 minutes to about 60 minutes. According to certain embodiments, the membrane is cured at a temperature of from about 120° C. to about 125° C. for a period of from about 20 minutes to about 30 minutes.

The resulting membrane can be washed to leach out any extractable in the membrane. Certain embodiments of the membrane, particularly a membrane having carboxyl functionality, are washed or leached in a basic solution, preferably at a pH of from about 8 to about 12. The leaching liquid can be prepared by adding a base such as sodium hydroxide, sodium carbonate, or sodium bicarbonate. The base can be added as a solid or a solution. Particular examples of pH's of the leaching liquid are about 11.9, about 11.4, and about 8.1. These pH's can be achieved by the use of, e.g., a 2N NaOH solution, sodium carbonate, or sodium bicarbonate.

Illustratively, a carboxylated membrane can be washed or leached at a temperature of from about 37° C. to about 93° C. or higher and preferably from about 54° C. to about 73° C. or higher. A sulfonic acid containing membrane can be washed or leached at a temperature of from about 54° C. to about 93° C. or higher. Embodiments of the membrane also can be leached in hot deionized water, e.g., deionized water held above 73° F. The washing or leaching can be carried out for a suitable length of time, for example, for about 20 to about 30 minutes or more. According to certain embodiments of the membrane, the washing or leaching can be carried out for about 1 hour or more. The resulting membrane is then dried in air or in an oven to remove the water.

The present invention provides a process for preparing a negatively charged microporous membrane comprising a porous substrate and a crosslinked coating having pendant anionic group. An embodiment of the process comprises:

(a) providing a porous substrate;
(b) contacting the substrate with a hydroxyl-rich material and a polymerized composition comprising an unsaturated monomer having an anionic group, at least one or more N-(hydroxyalkyl)- and/or N-(alkoxyalkyl)-acrylamides, a hydrophilic unsaturated monomer, and optionally an initiator;
(c) curing the substrate obtained in (b) to obtain the negatively charged membrane; and (d) optionally, extracting the membrane obtained in (c) to remove extractable residue therein.

The present invention further provides a negatively charged membrane comprising a porous substrate and a crosslinked coating. An embodiment of the process comprises:

(a) providing a porous substrate;
(b) contacting the substrate with a polysaccharide and a polymerized composition comprising an unsaturated monomer having an anionic group, an N-(hydroxymethyl)- and/or N-(alkoxymethyl)-acrylamides, and an initiator;
(c) curing the substrate obtained in (b) to obtain the negatively charged membrane; and (d) optionally, extracting the membrane obtained in (c) to remove extractable residue therein.

The present invention further provides, in an embodiment, a negatively charged microporous membrane comprising a porous support and a crosslinked coating wherein the crosslinked coating is prepared from a polymerized composition comprising an unsaturated monomer having an anionic group, an N-(hydroxymethyl)- or N-(alkoxymethyl)-acrylamide, a non-ionic hydrophilic acrylic monomer, and an initiator.

The present invention further provides, in another embodiment, a negatively charged microporous membrane comprising a porous substrate and a crosslinked coating prepared from a polysaccharide and a polymerized composition comprising an unsaturated monomer having an anionic group, an N-(hydroxymethyl)- or N-(alkoxymethyl)-acrylamide, and an initiator.

The present invention, in a further embodiment, provides a negatively charged microporous membrane comprising a porous substrate and a crosslinked coating prepared from a composition comprising an acrylic monomer having an anionic group, an N-(hydroxymethyl)- or N-(alkoxymethyl)-acrylamide, a nonionic hydrophilic acrylic monomer, and an initiator.

The present invention, in another embodiment, provides a negatively charged microporous membrane comprising a porous substrate and a crosslinked coating prepared from a polysaccharide and a polymerized composition comprising an acrylic monomer having an anionic group, an N-(hydroxymethyl)- or N-(alkoxymethyl)-acrylamide, and an initiator.

The present invention further provides a device e.g., a filter device, chromatography device, macromolecular transfer device, flow distributor arrangement, and/or a membrane module comprising one or more negatively charged membranes of the present invention. The device can be in any suitable form. For example, the device can include a filter element comprising the negatively charged membrane in a substantially planar or pleated form. In an embodiment, the element can have a hollow generally cylindrical form. If desired, the device can include the filter element in combination with upstream and/or downstream support or drainage layers. The device can include a plurality of membranes, e.g., to provide a multilayered filter element, or stacked to provide a membrane module, such as a membrane module for use in membrane chromatography. Filter cartridges can be constructed by including a housing and endcaps to provide fluid seal as well as at least one inlet and at least one outlet. The devices can be constructed to operate in crossflow or tangential flow mode as well as dead-end mode. Accordingly, the fluid to be treated can be passed, for example, tangentially to the membrane surface, or passed perpendicular to the membrane surface.

For embodiments of the membrane which are in the form of a tube or fiber, or bundles of tubes or fibers, the membrane can be configured as modules, e.g., after potting their ends with an adhesive. For a description of illustrative chromatographic devices, porous medium modules, and flow distributor arrangements, see U.S. Provisional Patent Application Nos. 60/121,667 and 60/121,701, both filed on Feb. 25, 1999; U.S. Provisional Patent Application Nos. 60/168,738 and 60/168,750, both filed on Dec. 6, 1999; and International Applications filed on Feb. 25, 2000 and entitled "Positively Charged Membrane" by Xiaosong Wu, Chung-Jen Hou, Jayesh Dharia, Peter Konstantin, and Yujing Yang; "Chromatography Devices and Flow Distributor Arrangements Used in Chromatography Devices" by Mark Hurwitz, Thomas Sorensen, John Stempel, and Thomas Fendya; and "Chromatography Devices, Porous Medium Modules Used in Chromatography Devices and Methods for Making Porous Medium Modules" by Mark Hurwitz, Thomas Fendya, and Gary Bush. See also UK Patent Application GB 2 275 626 A.

The membrane of the present invention has one or more advantageous properties, including high water permeability dynamic protein binding capacity, and charge density. Thus, for example, the membrane preferably has a water flow rate above 5 mL/min/cm$^2$, and preferably above 10 mL/min/cm$^2$, e.g., from about 20 mL/min/cm$^2$ to about 160 mL/min/cm$^2$, and preferably from about 25 mL/min/cm$^2$ to about 100 mL/min/cm$^2$ at 24 inch Hg. The membrane is robust and can withstand high treatment fluid flow rates. Thus, the membrane can be subjected to flow rates up to 10 cm/min, for example, from about 1 cm/min to 10 cm/min at 10 psi. The membrane has an open water bubble point of below about 70 psi, e.g., from about 2.5 psi to about 70 psi, and preferably from about 5 psi to about 50 psi.

The membrane of the present invention has a high charge density. The charge density of the membrane can be measured by methods known to those of ordinary skill in the art. For example, the charge density can be measured by the membrane's ability to bind a positively charged dye. Illustratively, the membrane has a Methylene Blue dye binding capacity of at least about 10 mL, e.g., from about 10 mL to about 1000 mL, and preferably from about 100 mL to about 800 mL, when tested with a 10 ppm dye solution in water. Methylene Blue is a positively charged dye. The dye binding capacity is measured by filtering under a 24 inch Hg negative pressure, a 10 ppm by weight solution, pH 6.6, of Methylene Blue dye in a membrane disc of 25 mm diameter, and monitoring the volume of the filtrate until a trace of the dye begins to appear in the filtrate.

The membrane of the present invention has a high specific protein binding capacity. The membrane has a lysozyme specific binding capacity of above 10 mg/mL, e.g., from about 10 mg/mL to about 130 mg/mL and preferably from about 25 mg/mL to about 120 mg/mL. The specific binding capacity can be determined by the following illustrative method. A fluid containing a lysozyme protein in 10 mM MES buffer, pH 5.5, is filtered by passing through a membrane at 1 cm/min and the concentration of the protein in the filtrate is measured as a function of time. The concentration of the protein can be determined spectrophotometrically, e.g., by measuring the absorbance of the protein at 280 nm. A breakthrough curve such as the one shown in FIG. 1 can then be constructed with the x-axis depicting the time of the filtration experiment and the y-axis depicting the protein concentration in the filtrate. The membrane has high specific protein binding capacity and low non-specific or hydrophobic binding. The slope of the breakthrough curve obtained on the membrane is vertical or substantially vertical. This characteristic offers improved resolution and separation of proteins. The membrane also has high dynamic protein binding capacity.

An advantage of the membrane of the present invention is that proteins do not leak prior to breakthrough. Another advantage of the present invention is that the components of the membrane are carefully chosen so that the membrane is free or substantially free of grafts or covalent links between the coating and the substrate. The preparation of negatively charged membranes of the present invention involves a chemistry and procedure that is relatively simple and easy to practice.

The properties of the membranes of the present invention make them attractive for use in the detection, separation, and/or purification of biomolecules such as proteins, amino acids, nucleic acids, and viruses. Examples of nucleic acids include modified or unmodified, synthetic or natural RNA and DNA.

The membranes of the present invention find use in various applications such as filtration of fluids containing positively charged atoms, molecules, and particulates, and macromolecular transfer from electrophoresis gels such as the transfer of nucleic acids and proteins from electrophoresis gels to an immobilizing matrix. The membrane can find use in the separation or purification of components present in biological fluids. Thus, for example, the membrane can find use in the purification of human albumins from the serum, in the therapeutic fractionation of blood, and separation of the components in genetically engineered cell cultures or fermentation broths. The membrane can be used in the purification of, for example, viral vaccines and gene therapy vectors such as adeno-associated viruses.

Accordingly, the present invention provides a process for treating a fluid containing biomolecules, the process comprising placing the fluid in contact with the negatively charged membrane. The positively charged materials adsorbed on the membrane can be recovered by eluting with a suitable solvent eluant. The present invention further provides a process for selectively adsorbing one or more biomolecules from fluid containing a mixture of biomolecules comprising contacting the fluid with the membrane under conditions favorable to the adsorption of selected biomolecules. The present invention further provides a process for selectively releasing one or more biomolecules from a membrane of the present invention comprising contacting the membrane having adsorbed biomolecules with an eluant under conditions favorable to the release of the selected biomolecules. The present invention further provides a process for macromolecular transfer from an electrophoresis gel comprising contacting a membrane of the present invention with the electrophoresis gel, and transferring the macromolecules from the gel to the membrane.

The negatively charged membrane of the present invention is particularly suitable for treating fluids containing biomolecules that have a positive surface charge for the given pH of the fluid. For example, lysozyme has an isoelectric point of 11.25, and it can be purified by using the negatively charged membrane of the present invention from a low salinity, for example 10 mM MES, fluid that is pH 5.5. Proteins with different surface charges may also be separated using the membrane of the present invention, for example separating lysozyme from Cytochrome C.

Thus, a mixture of lysozyme and Cytochrome C can be separated as follows. 80 $\mu$l of a fluid containing 3 mg/ml lysozyme and 1 Cytochrome C can be placed on a chromatographic column or stack of 5 layers of a 25 mm diameter negatively charged membrane of the present invention. The column or tack can be eluted under a gradient –7 ml from 10 mM MES buffer at a pH of 5.5 to 1M NaCl –10 mM MES buffer at a pH of 5.5. The flow rate can be 4 ml/min. Cytochrome C elutes first, followed by lysozyme.

The following examples further illustrate the present invention but should not be construed in any way limiting the scope of the invention.

EXAMPLE 1

This Example illustrates a method of preparing a polymer composition for preparing an embodiment of the negatively charged membrane of the present invention.

2-Acrylamido-2-methyl-1-propanesulfonic acid, N-(isobutoxymethyl)acrylamide, and hydroxypropyl methacrylate were combined in a weight ratio of 8.0:2.5:1.5 in a methanol-water medium to obtain a polymerization solution having a solids content of 12% by weight. Ammonium persulfate was used as the initiator at 0.3% by weight of the solution. The polymerization was carried out for a period of about 10–15 hours at ambient temperature (20–25° C.). The resulting solution had a viscosity of 166 cps.

EXAMPLE 2

This Example illustrates a method for preparing an embodiment of the negatively charged membrane of the present invention. This Example further illustrates the properties of that embodiment.

A coating solution was prepared by mixing the polymerization solution described in Example 1 and a water solution of dextran, molecular weight 148 K, so that the resulting solution contains polymer and dextran in the weight ratio of 3:1.

A hydrophilic microporous polyethersulfone substrate having a pore size of about 0.8 $\mu$m was coated with the above coating solution. The coated substrate was cured in an oven at 100–110° C. for 1 hour, followed by washing it in boiling DI water for 1 hour. The resulting membrane was dried in an oven to obtain an embodiment of the present invention.

The membrane obtained above was tested for treatment of a solution containing lysozyme. The solution was contained 206.4 $\mu$g per ml of 10 mM MES buffer at pH 5.5. The treatment fluid flow rate was 4 ml/min. Two membrane discs of 25 mm diameter were stacked together. The breakthrough curve obtained is set forth in FIG. 1. The membrane had a lysozyme binding capacity of 97 mg/ml. The relatively flat curve obtained during the first 10 minutes of the treatment confirmed that the membrane did not leak. The nearly vertical slope indicates that the membrane was capable of providing high resolution.

EXAMPLE 3

This Example illustrates a method for preparing an embodiment of the negatively charged membrane of the present invention. This Example further illustrates the properties of that embodiment.

A coating solution was prepared by mixing the polymerization solution described in Example 1 and a water solution of dextran, molecular weight 148 K, so that the resulting solution contains polymer and dextran in the weight ratio of 4:1.

A hydrophilic microporous cellulose nitrate substrate having a pore size of about 0.8 $\mu$m was coated with the above coating solution. The coated substrate was cured in an oven at 100–110° C. for 1 hour, followed by washing it in boiling DI water for 1 hour. The resulting membrane was dried in an oven to obtain an embodiment of the present invention.

Figure 2:
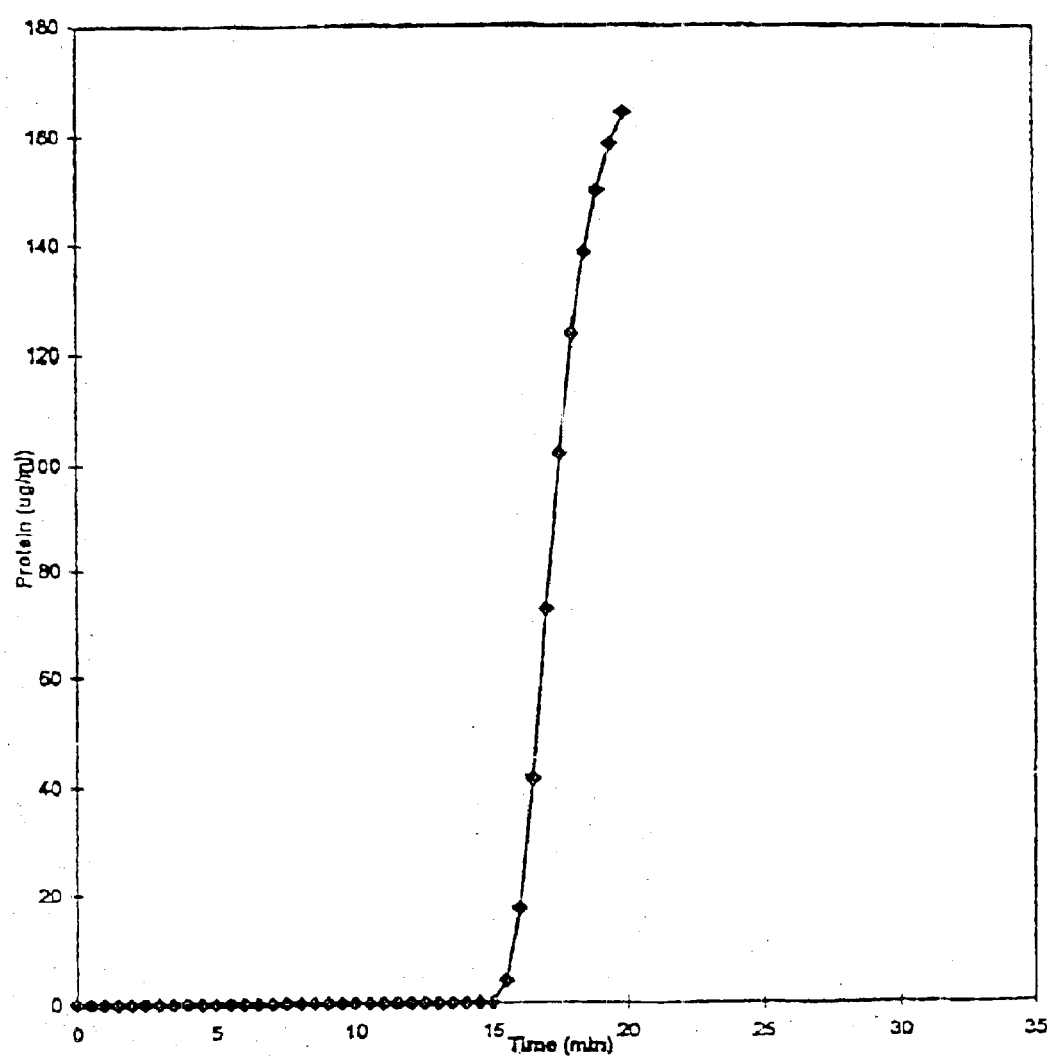
FIG. 2 depicts the breakthrough curve for lysozyme obtained on another embodiment membrane of the present invention. The x-axis and y-axis are as described in FIG. 1. See Example 3 for additional details.

The membrane obtained above was tested with a solution containing lysozyme. The solution was contained 201.3 $\mu$g per ml of 10 mM MES buffer at pH 5.5. The treatment fluid flow rate was 4 ml/min. Two membrane discs of 25 mm diameter were stacked together. The breakthrough curve obtained is set forth in FIG. 2. The membrane had a lysozyme binding capacity of 77 mg/ml. The relatively flat curve obtained during the first 10 minutes of the treatment confirmed that the membrane did not leak. The nearly vertical slope indicates that the membrane was capable of providing high resolution.

EXAMPLE 4

This Example illustrates a method for preparing another embodiment of the negatively charged membrane of the present invention. This Example further illustrates the properties of that embodiment.

2-Acrylamidoglycolic acid, 2-carboxyethyl acrylate, N-(isobutoxymethyl)acrylamide, N-(hydroxymethyl)-acrylamide, and hydroxypropyl acrylate were combined in a weight ratio of 5.0:5.0:3.0:1.5:1.5 in a methanol-water medium to obtain a polymerization solution having a solids content of 16% by weight. Ammonium persulfate was used as the initiator at 0.4% by weight of the solution. The polymerization was carried out for a period of about 16–24 hours at ambient temperature. The resulting solution had a viscosity of 116 cps. A coating solution was prepared by mixing the polymerization solution and a water solution of dextran, molecular weight 148 K, so that the resulting solution contained 4% polymer and 1.33% dextran by weight.

A hydrophilic microporous polyethersulfone substrate having a pore size of about 0.8 $\mu$m was coated with the above coating solution. The coated substrate was cured in an oven at 100–110° C. for 1 hour, followed by washing it in boiling DI water for 1 hour. The resulting membrane was dried in an oven to obtain another embodiment of the present invention.

Figure 3:
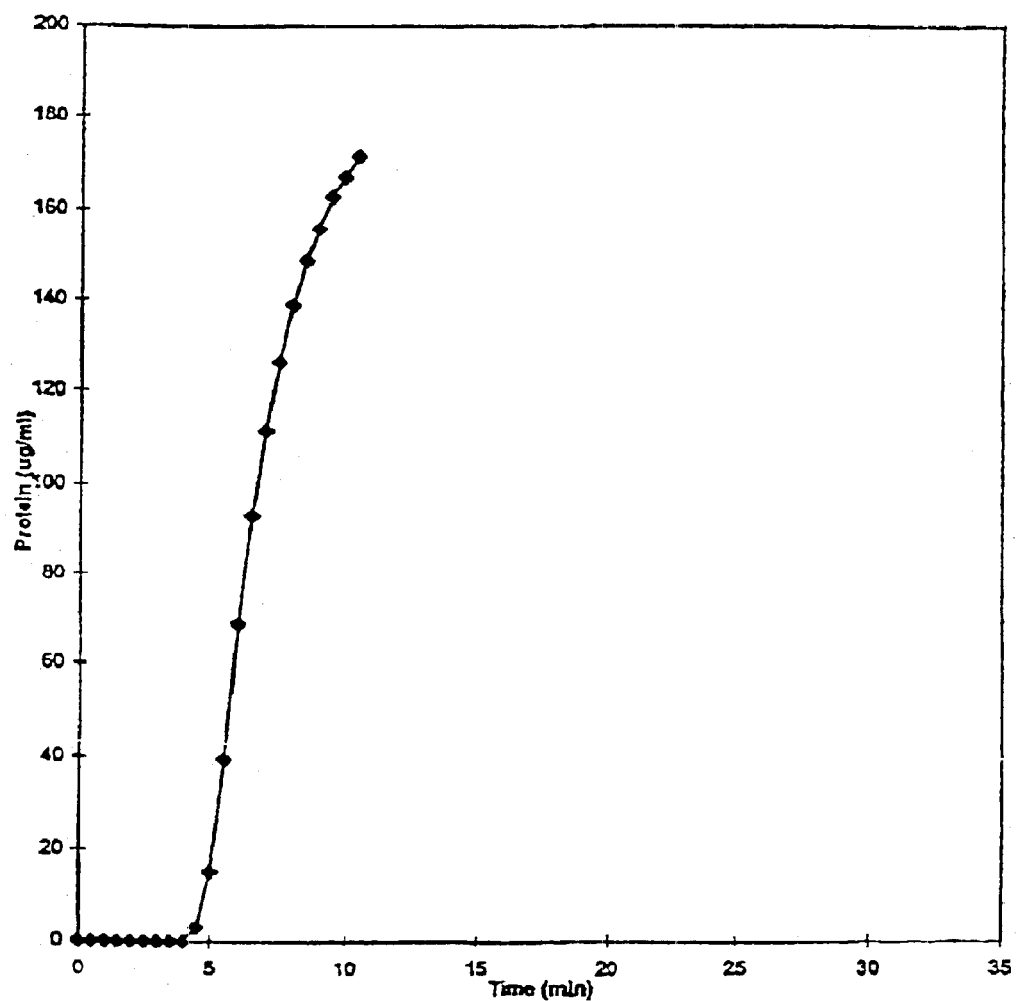
FIG. 3 depicts the breakthrough curve for lysozyme obtained on another embodiment membrane of the present invention. The x-axis and y-axis are as described in FIG. 1. See Example 4 for additional details.

The membrane obtained above was tested with a solution containing lysozyme. The solution was contained 213.6 $\mu$g per ml of 10 mM MES buffer at pH 5.5. The treatment fluid flow rate was 4 ml/min. Two membrane discs of 25 mm diameter were stacked together. The breakthrough curve obtained is set forth in FIG. 3. The membrane had a lysozyme binding capacity of 45 mg/ml. The relatively flat curve obtained during the first 10 minutes of the treatment confirmed that the membrane did not leak. The nearly vertical slope indicates that the membrane was capable of providing high resolution.

All references cited herein, including patents, patent applications, and publications, are incorporated by reference in their entireties.

While this invention has been described with an emphasis upon several embodiments, it will be obvious to those of ordinary skill in the art that variations of the embodiments may be used and that it is intended that the invention may be practiced otherwise than as specifically described herein. Accordingly, this invention includes all modifications encompassed within the spirit and scope of the invention as defined by the following claims.

What is claimed is:

1. A filter element comprising at least one negatively charged microporous membrane comprising a porous substrate and a crosslinked coating, wherein the crosslinked coating is prepared from a solution comprising a polysaccharide and an anionic polymer, the anionic polymer being obtained by polymerizing a mixture comprising an unsaturated monomer having a negatively charged group, a hydrophilic non-ionic unsaturated monomer, and at least one or more N-(hydroxyalkyl)- or N-(alkoxyalkyl)-acrylamide monomers, wherein the crosslinked coating comprises amide-ester and amide—amide crosslinks.

2. The filter element of claim 1, wherein the negatively charged microporous membrane comprises a pleated membrane.

3. The filter element of claim 1, having a hollow, generally cylindrical form.

4. The filter element of claim 2, comprising a plurality of pleated negatively charged microporous membranes.

5. The filter element of claim 2, having a hollow, generally cylindrical form.

6. The filter element of claim 4, having a hollow, generally cylindrical form.

7. The filter element of claim 1, comprising a plurality of negatively charged microporous membranes.

8. The filter element of claim 7, having a hollow, generally cylindrical form.

9. A device comprising a housing comprising at least one inlet and at least one outlet and defining a fluid flow path between the inlet and the outlet, and, interposed between the inlet and the outlet and across the fluid flow path, at least one negatively charged microporous membrane comprising a porous substrate and a crosslinked coating, wherein the crosslinked coating is prepared from a solution comprising a polysaccharide and an anionic polymer, the anionic polymer being obtained by polymerizing a mixture comprising an unsaturated monomer having a negatively charged group, a hydrophilic non-ionic unsaturated monomer, and at least one or more N-(hydroxyalkyl)- or N-(alkoxyalkyl)-acrylamide monomers, wherein the crosslinked coating comprises amide-ester and amide—amide crosslinks.

10. A device for tangential flow filtration comprising a housing comprising an inlet and a first outlet and a second outlet;

the device defining a first fluid flow path between the inlet and the first outlet, and defining a second fluid flow path between the inlet and the second outlet, and, interposed between the inlet and the first outlet and across the first fluid flow path; and, interposed between the inlet and the first outlet and across the first fluid flow path, and interposed between the inlet and the second outlet and tangential to the second fluid flow path, at least one negatively charged microporous membrane comprising a porous substrate and a crosslinked coating, wherein the crosslinked coating is prepared from a solution comprising a polysaccharide and an anionic polymer, the anionic polymer being obtained by polymerizing a mixture comprising an unsaturated monomer having a negatively charged group, a hydrophilic non-ionic unsaturated monomer, and at least one or more N-(hydroxyalkyl)- or N-(alkoxyalkyl)acrylamide monomers, wherein the crosslinked coating comprises amide-ester and amide—amide crosslinks.

11. The device of claim 9, comprising a plurality of negatively charged microporous membranes, each membrane comprising a porous substrate and a crosslinked coating, wherein the crosslinked coating is prepared from a solution comprising a polysaccharide and an anionic polymer, the anionic polymer being obtained by polymerizing a mixture comprising an unsaturated monomer having a negatively charged group, a hydrophilic non-ionic unsaturated monomer, and at least one or more N-(hydroxyalkyl)- or N-(alkoxyalkyl)acrylamide monomers, wherein the crosslinked coating comprises amide-ester and amide—amide crosslinks, interposed between the inlet and the outlet and across the fluid flow path.

12. The device of claim 9, wherein the negatively charged microporous membrane comprises a pleated membrane.

13. The device of claim 9, including a filter element having a hollow, generally cylindrical form, wherein the filter element comprises the at least one negatively charged microporous membrane.

14. The device of claim 11, wherein the plurality of negatively charged microporous membranes comprise pleated membranes.

15. The device of claim 11, including a filter element having a hollow, generally cylindrical form, wherein the filter element comprises the plurality of negatively charged microporous membranes.

16. The device of claim 15, wherein the plurality of negatively charged microporous membranes comprise pleated membranes.

* * * * *